(12) United States Patent
Gartner et al.

(10) Patent No.: US 9,211,369 B2
(45) Date of Patent: Dec. 15, 2015

(54) COMPACT INTEGRATED BLOOD PUMP OXYGENATOR OR GAS TRANSFER DEVICE WITH HYDROGEL IMPELLER PACKING MATERIAL AND ROLLOVER IMPELLER OUTLET

(71) Applicant: Ension, Inc., Pittsburgh, PA (US)

(72) Inventors: Mark J Gartner, Pittsburgh, PA (US); Brian J Fill, Pittsburgh, PA (US); Patrick Cahalan, Cape Coral, FL (US); Linda Cahalan, Cape Coral, FL (US); Jeffrey W. Speakman, Saxonburg, PA (US)

(73) Assignee: Ension, Inc, Pittsburgh, PA (US)

( * ) Notice: Subject to any disclaimer, the term of this patent is extended or adjusted under 35 U.S.C. 154(b) by 192 days.

(21) Appl. No.: 13/916,739

(22) Filed: Jun. 13, 2013

(65) Prior Publication Data

US 2013/0343954 A1    Dec. 26, 2013

Related U.S. Application Data

(60) Provisional application No. 61/659,416, filed on Jun. 13, 2012.

(51) Int. Cl.
*A61M 1/16* (2006.01)
*A61M 1/10* (2006.01)

(52) U.S. Cl.
CPC .............. *A61M 1/1698* (2013.01); *A61M 1/101* (2013.01); *A61M 1/1006* (2014.02)

(58) Field of Classification Search
CPC . A61M 1/1006; A61M 1/101; A61M 1/1013; A61M 1/1015; A61M 1/1017; A61M 1/1031; A61M 1/1036; A61M 1/1698
See application file for complete search history.

(56) References Cited

U.S. PATENT DOCUMENTS

| | | | |
|---|---|---|---|
| 3,998,593 A | 12/1976 | Yoshida et al. | |
| 4,490,331 A | 12/1984 | Steg, Jr. | |
| 4,639,353 A | 1/1987 | Takemura et al. | |
| 4,975,247 A | 12/1990 | Badolato et al. | |
| 5,017,103 A * | 5/1991 | Dahl | 417/420 |
| 5,217,689 A | 6/1993 | Raible | |
| 5,263,924 A | 11/1993 | Mathewson | |
| 5,266,265 A | 11/1993 | Raible | |
| 5,270,005 A | 12/1993 | Raible | |
| 5,429,486 A | 7/1995 | Schock et al. | |
| 5,658,136 A * | 8/1997 | Mendler | 417/420 |
| 5,770,149 A | 6/1998 | Raible | |
| 5,830,370 A | 11/1998 | Maloney, Jr. et al. | |
| 6,217,826 B1 | 4/2001 | Reeder et al. | |
| 6,302,910 B1 * | 10/2001 | Yamazaki et al. | 623/3.1 |
| 6,503,450 B1 | 1/2003 | Afzal et al. | |

(Continued)

*Primary Examiner* — Philip R Wiest
*Assistant Examiner* — Benjamin Klein
(74) *Attorney, Agent, or Firm* — Blynn L. Shideler; Krisanne Shideler; BLK Law Group (57) ABSTRACT

An integrated blood pump oxygenator comprises an impeller housing supporting an impeller with an annular hydrogel impeller packing material adjacent the bearings and around the shaft of the impeller. The oxygenator including a rollover outlet in the form of an annular chamber extending around a center pump housing member; and further including an annular chamber within an annular array of hollow fiber membranes in fluid communication with the annular chamber extending from the impeller around the center pump housing; wherein the annular chamber provides substantially perpendicular radial outward cross flow across the membranes.

20 Claims, 4 Drawing Sheets

(56) References Cited

U.S. PATENT DOCUMENTS

| | | |
|---|---|---|
| 6,723,284 B1 | 4/2004 | Reeder et al. |
| 6,730,267 B2 | 5/2004 | Stringer et al. |
| 6,929,777 B1 | 8/2005 | Litwak et al. |
| 6,963,222 B1 | 11/2005 | Davies, Jr. |
| 7,122,155 B2 | 10/2006 | Waterbury et al. |
| 7,927,544 B2 | 4/2011 | Federspiel et al. |
| 2002/0057989 A1 | 5/2002 | Afzal et al. |
| 2002/0110485 A1* | 8/2002 | Stringer et al. ............ 422/45 |
| 2004/0219059 A1 | 11/2004 | Barringer et al. |
| 2007/0249888 A1 | 10/2007 | Wu et al. |
| 2008/0190870 A1 | 8/2008 | Schoeb |
| 2008/0199357 A1* | 8/2008 | Gellman et al. ............ 422/48 |
| 2009/0175762 A1 | 7/2009 | Ogihara et al. |
| 2010/0101657 A1 | 4/2010 | Morley et al. |
| 2010/0288703 A1 | 11/2010 | Fortenberry |

* cited by examiner

FIG. 4

COMPACT INTEGRATED BLOOD PUMP OXYGENATOR OR GAS TRANSFER DEVICE WITH HYDROGEL IMPELLER PACKING MATERIAL AND ROLLOVER IMPELLER OUTLET

RELATED APPLICATIONS

This application claims priority to United States provisional patent application Ser. No. 61/659,416 filed Jun. 13, 2012, entitled "Compact Integrated Blood Pump Oxygenator with Hydrogel Impeller Packing Material and Rollover Impeller Outlet."

BACKGROUND OF THE INVENTION

1. Field of the Invention

The present invention relates to a heat and mass transfer mechanism, more specifically to compact integrated blood pump oxygenators.

2. Background Information

U.S. patent application Publication No. 2008-0199357, which is incorporated herein by reference, also relates to an integrated centrifugal blood pump-oxygenator having a rotational body being rotatably arranged in a rotor-housing of the bottom. According to the invention disclosed in U.S. patent application Publication No. 2008-0199357, the rotational body is magnetically journalled in a contact free manner with respect to the rotor-housing. U.S. Patent Application Publication Number 2008-0199357 provides an generally accurate backdrop for describing the field of integrated centrifugal blood pump-oxygenators.

As reported in U.S. patent application Publication No. 2008-0199357 lung diseases are the third largest cause of death in the United States of America, accounting for approximately 1 out of every 7 adult deaths. It has been estimated that 30 million Americans are living with chronic lung disease. Adult respiratory distress syndrome (ARDS) has been reported to afflict approximately 150,000 patients annually in the U.S, and despite advances in critical care, mortality remains around 40-50%. Currently available therapies for patients with chronic respiratory failure include, for example, ventilation and extracorporeal membrane oxygenation (ECMO). In intensive care medicine, extracorporeal membrane oxygenation (ECMO) is an extracorporeal technique of providing both cardiac and respiratory support oxygen to patients whose heart and lungs are so severely diseased or damaged that they can no longer serve their function.

ECMO systems are attractive since they closely simulate physiological gas exchange. Attempts have been made to integrate multiple components of cardiopulmonary, ECMO-systems into single structures so as to eliminate or minimize the need for the extension of lengthy, blood-filled tubes. Various integrated pump-oxygenators have been described as discussed in U.S. Pat. Nos. 5,217,689; 5,266,265; 5,270,005; 5,770,149; 4,975,247; 5,429,486; 6,963,222; and 6,730,267, which are incorporated herein by reference.

U.S. patent application Publication No. 2008-0199357 suggests there are drawbacks associated with many of these integrated pump-oxygenators, including non-uniform blood flow through the fiber membranes and the existence of laminar boundary flow zones between blood cells and fiber membranes. Non-uniform blood flow across the fiber membranes results in hyper- and hypo-perfusion of the blood in flow paths. U.S. patent application Publication No. 2008-0199357 discusses efforts to decrease the effect of the boundary layer include increasing shear rate and/or turbulence of the blood flow path by the introduction of secondary flows, for example, by directing blood to flow at a substantial angle, such as perpendicular, to the fiber membranes. U.S. Pat. No. 4,639,353, which is incorporated herein by reference, discloses the use of an arrangement of bundles of hollow fibers perpendicular to the direction of blood flow via a series of flow guide structures. U.S. Pat. No. 5,263,924, which is incorporated herein by reference, discloses the use of an integrated centrifugal pump and membrane oxygenator comprising hollow fibers, which are displaced circumferentially in a ring around an impeller of the centrifugal pump and through which blood is pumped for oxygenation. See also U.S. Pat. No. 3,998,593 issued to and U.S. Pat. No. 4,490,331 which are incorporated herein by reference.

Other efforts to decrease the effect of the boundary layer include actively rotating hollow fiber membranes or moving fiber membranes in the path of blood flow, examples of which are described in U.S. Pat. Nos. 5,830,370; 6,217,826; 6,503,450; 6,723,284; and 7,122,155, which are incorporated herein by reference.

Additional patents and publications giving a general overview of conventional blood pump-oxygenators include U.S. Pat. No. 6,929,777, 7,927,544, U.S. Publication Nos. 2002-0057989, 2004-0219059, 2007-0249888, 2008-0190870, 2009-0175762, 2010-0101657, and 2010-0288703 which are incorporated herein by reference.

Despite improvements in the performance and design of conventional blood pump-oxygenators, there remains a need for a more compact and efficient blood-pump oxygenator with less pronounced or fewer drawbacks. Thus, there is a need for a compact, efficient and minimally-traumatic pump-oxygenator. It is an object of the present invention to provide such an improved blood pump-oxygenator. This and other objects and advantages, as well as additional inventive features, will become apparent the detailed description provided herein.

SUMMARY OF THE INVENTION

One aspect of this invention is directed to an integrated blood pump oxygenator comprising a central housing member defining a central blood flow path extending along a general longitudinal axis of the integrated blood pump oxygenator; a center pump housing member coupled to the central housing member and defining a pump inlet in fluid communication with the central blood flow path; an impeller rotationally received within the area of the pump inlet formed by the central pump housing member, wherein the impeller, inlet and center pump housing member combine to form a centrifugal pump; an impeller housing supporting the impeller and wherein the impeller housing and center pump housing member combine to form a rollover outlet in the form of an annular chamber extending around the center pump housing member; an outer housing coupled to the center pump housing; an annular array of hollow fiber membranes configured for gas transfer within the outer housing; and an annular chamber within the annular array of hollow fiber membranes in fluid communication with the annular chamber extending from the impeller around the center pump housing; wherein the annular chamber provides substantially perpendicular radial outward cross flow across the membranes.

Another aspect of this invention is directed to an integrated blood pump oxygenator comprising an outer housing; a center pump housing member defining a pump inlet; an impeller rotationally received within the area of the pump inlet formed by the central pump housing member, wherein the impeller, inlet and center pump housing member combine to form a centrifugal pump; an impeller housing supporting the impeller; a stationary shaft coupled to the impeller housing; bearings between the shaft and the impeller, wherein the impeller is rotationally mounted to the stationary shaft; an annular hydrogel impeller packing material adjacent the bearings and around the shaft; and an annular array of hollow fiber membranes configured for gas transfer within the outer housing, and configured such that flow from the centrifugal pump flows over the hollow fiber membranes.

These and other advantages are described in the brief description of the preferred embodiments in which like reference numeral represent like elements throughout.

DESCRIPTION OF THE PREFERRED EMBODIMENTS

Figures 1, 2:
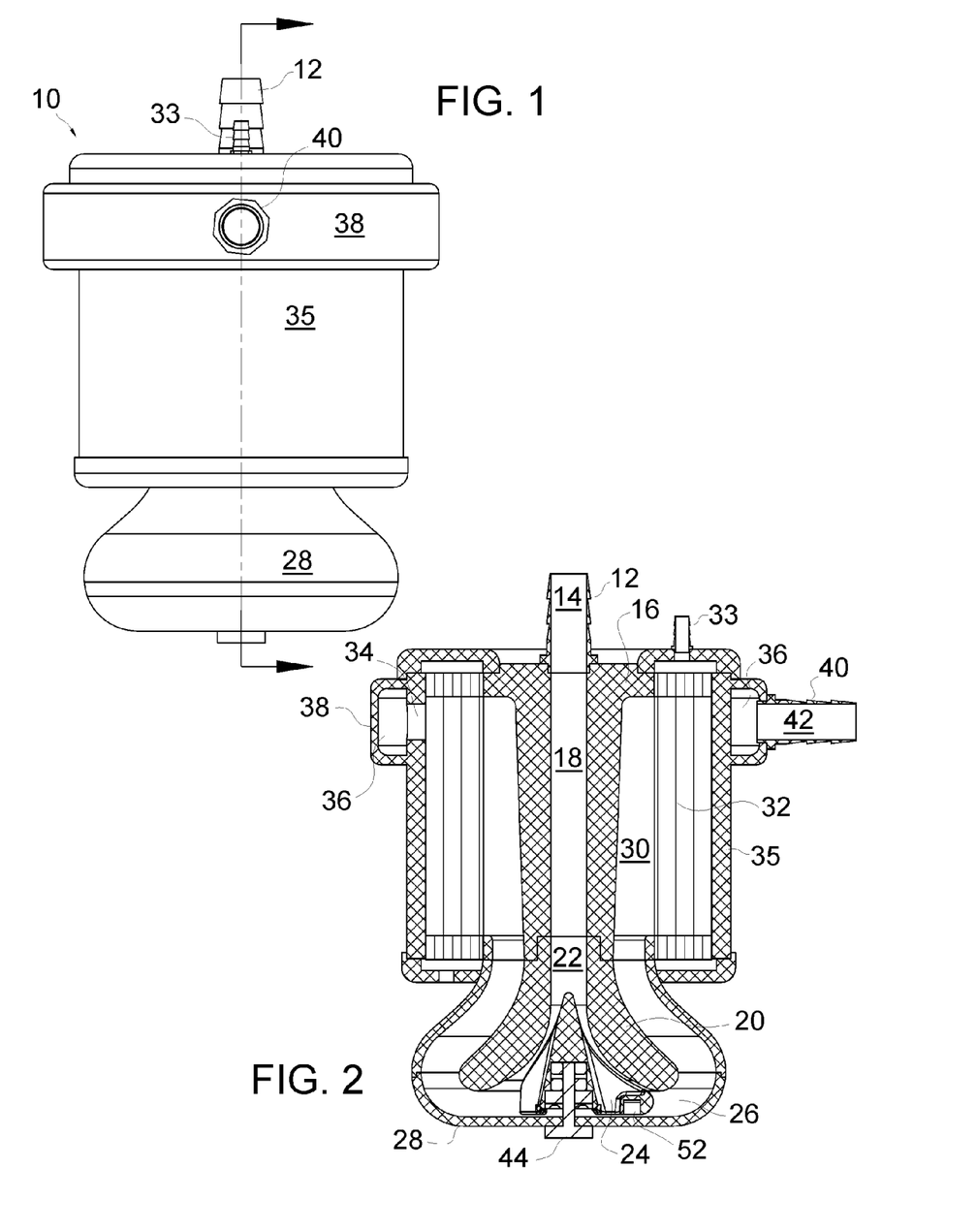
FIG. 1 is a schematic side elevation view of a compact integrated blood pump oxygenator with hydrogel impeller packing material and rollover impeller outlet in accordance with one aspect of the present invention.
FIG. 2 is a schematic side section view of the compact integrated blood pump oxygenator of FIG. 1.

The general operational details of a heat and mass transfer mechanism, such as an integrated blood pump oxygenators are extremely well known in the art, as fully described in the above cited patents and published patent applications that are incorporated herein by reference. The present invention, shown in schematic side elevation view in FIG. 1, is directed toward the compact construction of an integrated blood pump oxygenator 10 providing radially inside out flow across the membranes 32, which flow comes from a rollover impeller outlet forming an annular channel 26 extending to annular chamber 30 within the membranes 32; and toward a hydrogel impeller packing material 48 in accordance with one aspect of the present invention. These aspects are better understood in connection with the figures and the following description.

FIG. 2 is a schematic side section view of the compact integrated blood pump oxygenator of FIG. 1 and illustrates a blood inlet coupling 12 defining a blood inlet path 14 extending along a general longitudinal axis of the integrated blood pump oxygenator 10. The coupling 12 is attached to central housing member 16 defining a central blood flow path 18 in fluid communication with the blood inlet path 14 and extending along a general longitudinal axis of the integrated blood pump oxygenator 10.

The central housing member 16 is coupled to a center pump housing member 20 defining a pump inlet 22 in fluid communication with the central blood flow path 18. An impeller 24 is rotationally received within the area of the pump inlet 22 formed by the diverging central pump housing member 20 as shown. The impeller 24 inlet 22 and center pump housing member 20 combine to form a "centrifugal pump" which is generally defined as a rotodynamic pump that uses a rotating impeller, such as impeller 24, to increase the pressure and flow rate of a fluid, in this case blood. Centrifugal pumps are well understood and are the most common type of pump used to move liquids, here blood, through a system. The fluid typically enters the pump impeller along or near to the rotating axis, as here with inlet 22, and is accelerated by the impeller, impeller 24 in this case, flowing radially outward (or axially, and in this case both) into a diffuser or volute chamber, from where it exits into the downstream system as described below.

Figure 4:
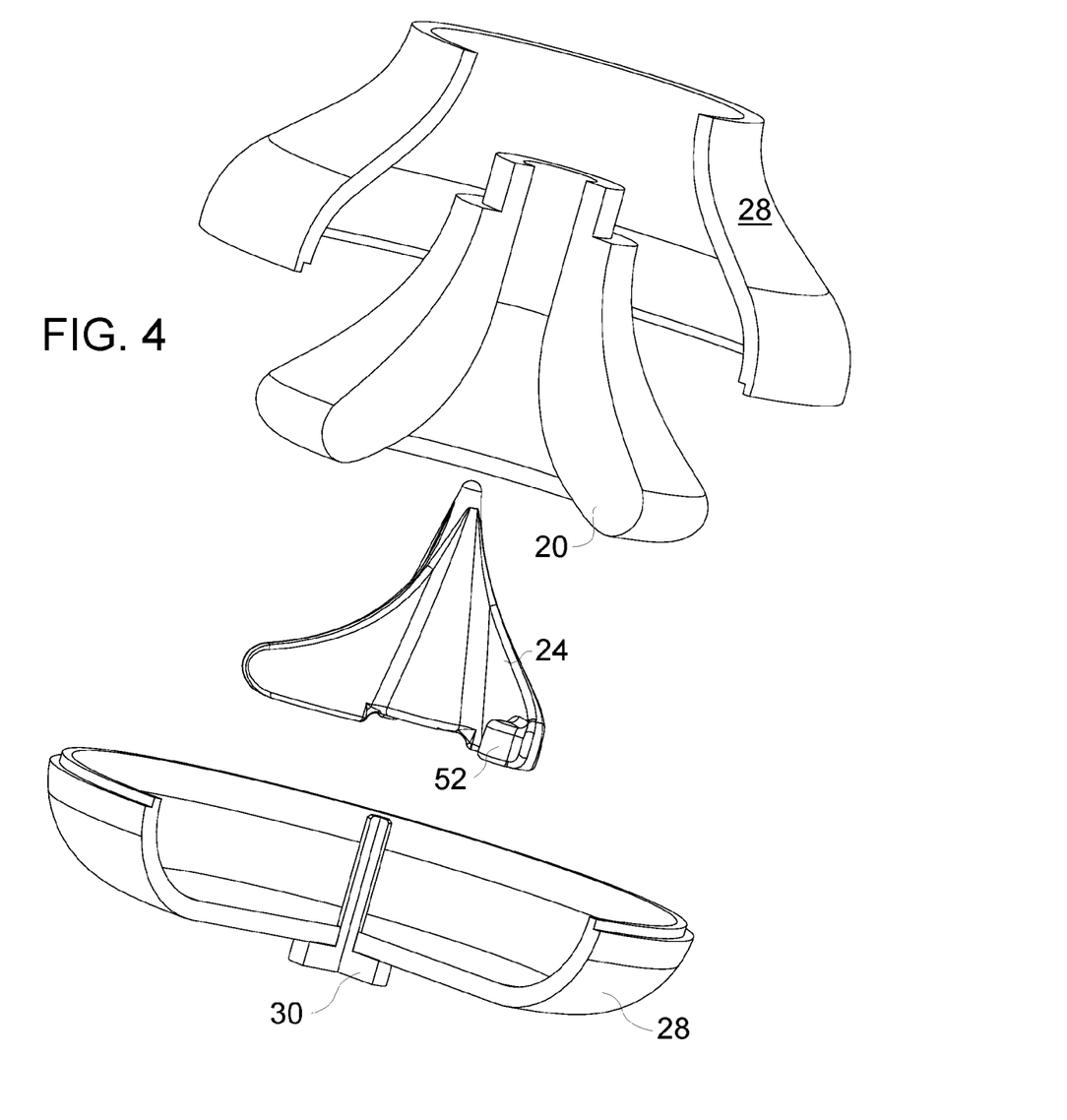
FIG. 4 is an exploded perspective view of an impeller housing and impeller of the integrated blood pump oxygenator of FIG. 1.

The impeller is rotationally mounted as will described in detail below on an outer impeller housing 28, which may be formed as two pieces for easy assembly. FIG. 4 is an exploded perspective view of the impeller housing 28 and impeller 24 of the integrated blood pump oxygenator 10 of FIG. 1. The impeller housing 28 and center pump housing member 20 combine to form a rollover outlet 26, also called a rollover diffuser. The rollover outlet 26 is an annular chamber extending around the center pump housing member 20 to the annular chamber 30 within the annular array of hollow fiber membranes 32. The annular chamber 30 extends the substantial length of the membranes 32 outside of the central housing member 16, as shown providing for efficient perpendicular radial outward cross flow across membranes 32.

The construction and operation of the individual hollow fiber membranes 32 in an oxygenator are well known in the art, and are also referred to as membrane hollow fibers, or fiber bundles, or merely tubes. These hollow fiber membranes 32 may be made out of polymethylpentene, polypropylene or silicone, for example. The hollow fiber membranes 32 are not discussed in detail herein nor are the sweep gas inlet 33 and outlet (not shown), nor the operation of the sweep gasses, as the construction and operation of these elements, per se, are conventional. The membranes 32 are contained within a generally cylindrical housing 35, which is coupled to the impeller housing 28.

Figure 5:
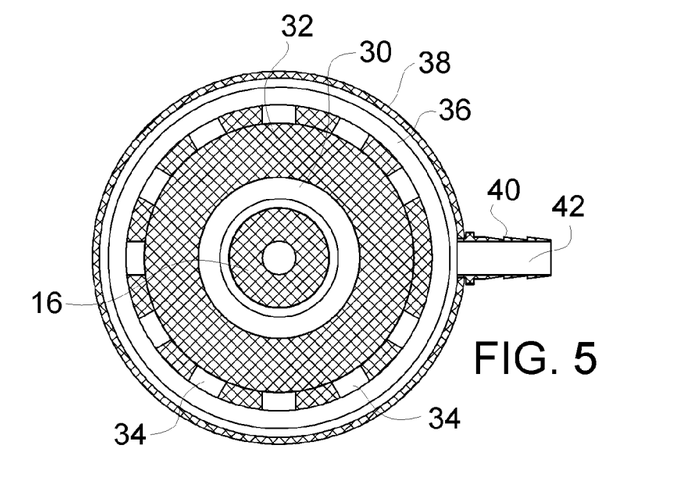
FIG. 5 is a cross section view of outlet housing of the integrated blood pump oxygenator of FIG. 1.

FIG. 5 is a cross section view of an outlet housing 38 coupled to housing 35, also called outer housing 35, and defining an annular outlet opening 36 of the integrated blood pump oxygenator 10. The oxygenated blood can flow to the annular outlet opening 36 through a series of communication openings 34 in cylindrical housing 35 as shown best in FIG. 5. A blood outlet coupling 40 is coupled to the outlet housing 38 and defines a blood outlet path 42 extending downstream of the integrated blood pump oxygenator 10.

The compact arrangement described for the integrated blood pump oxygenator 10 provides efficient, radial, inside out flow of the blood across the membranes 34. As should be apparent the blood flow through the integrated blood pump oxygenator 10 is from upstream of the integrated blood pump oxygenator 10 into the inlet path 14 and the central blood flow path 18 extending along a general longitudinal axis of the integrated blood pump oxygenator 10 to the pump inlet 22, and then through or via impeller 24 to the annular rollover outlet 26 extending around the center pump housing member 20 to the annular chamber 30, then radial outwardly across the membranes 34 for oxygenation and through openings 34 to annular outlet opening 36 and then through blood outlet path 42 to downstream of the integrated blood pump oxygenator 10.

Figure 3:
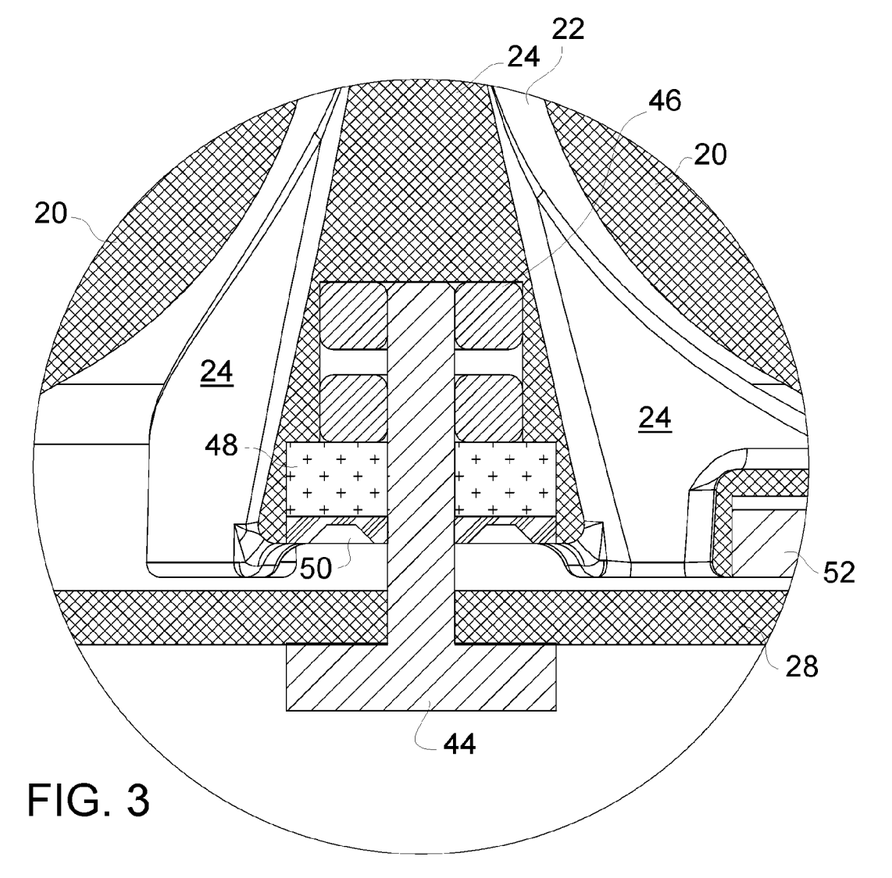
FIG. 3 is an enlarged schematic side elevation view of an impeller mount of the integrated blood pump oxygenator of FIG. 1.

Another significant aspect of the present invention relates to the rotational mounting of the magnetically driven impeller 24. FIG. 3 is an enlarged schematic side elevation view of this mounting of the impeller 24 to the housing 28 in the integrated blood pump oxygenator 10. The impeller 24 is rotationally mounted to a stationary shaft 44 coupled to housing 28. The shaft is shown extending through the housing 28, but as the shaft 44 is stationary it can be within the housing 28 as well.

The mounting structure includes conventional bearings 46 between the shaft 44 and the impeller 24. The mounting structure according to the invention further includes an annular hydrogel impeller packing material 48 adjacent the bearings 46 and around the shaft 44. A hydrogel can be generally described as the formation of a colloid in which the disperse phase (colloid) has combined with the continuous phase (water) to produce a viscous jellylike product. As a more detailed discussion, a hydrogel, sometimes called an aqua-gel, is a network of polymer chains that are hydrophilic, which are often found as a colloidal gel in which water is the dispersion medium. Hydrogels are often highly absorbent natural or synthetic polymers as they can contain over 99.9% water. Hydrogels also possess a degree of flexibility very similar to natural tissue, due to their significant water content.

Adjacent the annular hydrogel impeller packing material 48 is a conventional seal 50 press fit into place. The inclusion of the annular hydrogel impeller packing material 48 substantially improves the operation of seal 50 and extends the life and efficiency of the bearings 46. The construction of the hydrogel is described in detail below.

Figures 6, 7:
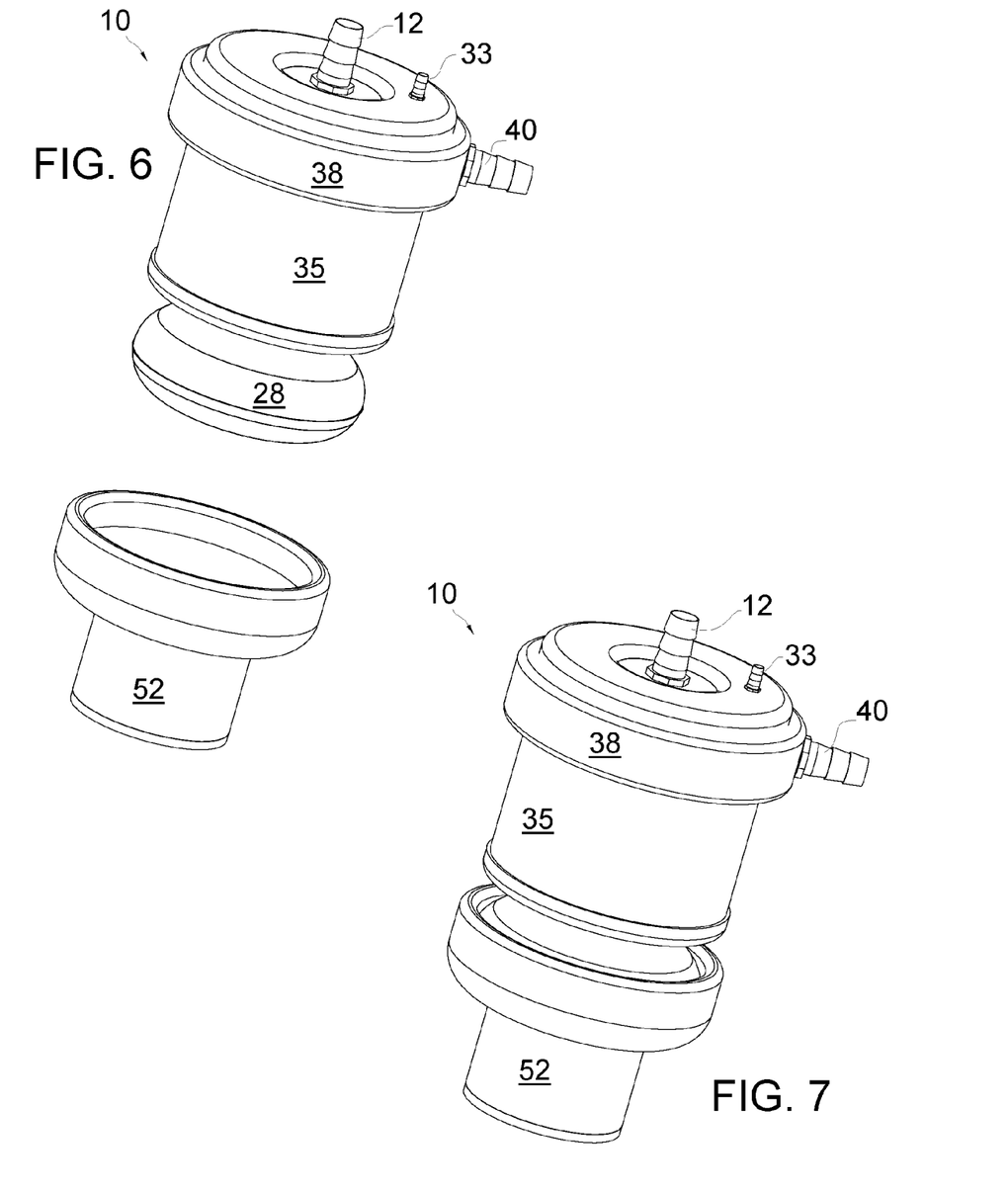
FIG. 6 is a schematic exploded perspective view of the compact integrated blood pump oxygenator of FIG. 1 and associated magnetic drive.
FIG. 7 is a schematic view of the compact integrated blood pump oxygenator of FIG. 1 and associated magnetic drive of FIG. 6.

The integrated blood pump oxygenator 10 is a completely sealed oxygenator 10 utilizing a magnetic drive 52. FIG. 6 is a schematic exploded perspective view of the compact integrated blood pump oxygenator 10 of FIG. 1 and associated magnetic drive 52, and FIG. 7 is a schematic view of the compact integrated blood pump oxygenator of FIG. 1 and associated magnetic drive of FIG. 6. The power from the motor in magnetic drive 52 is transmitted to the centrifugal impeller 24 by means of a magnetic coupling via magnets 52 integrated into the impeller 24 as best shown in FIG. 3. With the use of a magnetic drive 52 the housing 28 forms a so called isolation shell between the drive magnet and the impeller magnet 52 and completely separates the liquid side from the drive side in the integrated blood pump oxygenator 10.

The integrated blood pump oxygenator 10 could, alternatively, use a direct drive in which case shaft 44 would be rotating with the impeller 24 and the sealing arrangement, using conventional bearings 46, hydrogel packing material 48 and seal 50 would be between the rotating shaft 44 and the housing 28, with the seal 50 facing the blood side of the housing 28.

A number of hydrogel formulations are possible for forming suitable hydrogel packing material 48 including glycerol-impregnated hydrogel formulation. The following examples illustrate suitable hydrogel formulations to use as the barrier/spacer of the annular hydrogel packing material 48 which hugs the bearing shaft 44 to help prevent leaking between the seal 50 in the impeller bearing assembly of bearings 46.

Hydrogel Examples Setup and Procedure:
Initiator/Catalyst*
Potassium persulfate (Per) 0.095 g/25 ml DI
Potassium bisulfate (Bi) 0.095 g/25 ml DI
Ferrous sulfate (Fe) 0.060 g/25 ml DI
The above catalyst solutions are diluted 10×=1 ml in 9 ml DI
Catalyst is made fresh daily
1% Methylenebis(acrylamide) (MBA) X-Linker
0.2 g (MBA) in 20 ml DI
Hydrogel Formulation (1)
100 ml tri-pour beaker
12.5 g of acrylamide monomer were dissolved in 7.5 g DI $H_2O$ by placing in a warm water bath ~40° C. under stirring for 10 min.
The dissolved AAm solution was then removed from the water bath and 5 g of glycerol was added, cover and start degassing/purge with Argon and continue stirring for 5 min.
Add 500 µl of 1% MBA, continue purge and stirring for 5-7 min.
Remove purge line and connect to the covered mold vessel (200 ml PP container)
Pipette 250 µl of each diluted catalyst (Per/Bi/Fe) into a 1 ml vial then dispense into the hydrogel solution
Stir for ~15-20 seconds to incorporate and quickly pour into the mold under Argon atmosphere.

Condensation from the polymerized hydrogel was observed within 2 min., purging continued for 10 min. after which the hydrogel was removed from the mold and placed on non-stick backing.

Observations: Overall the hydrogel looked good only a few bubbles were observed, the gel was not sticky. Dimension's were 8.5 cm in diameter and ~4.3 mm thick. One 8 mm diameter sample was cut from the hydrogel using a punch.

Hydrogel Formulation (2) with Scrim/Reinforcement
100 ml tri-pour beaker
12.5g of acrylamide monomer were dissolved in 7.5 g DI $H_2O$ by placing in a warm water bath ~40° C. and stirring for 10 min.
The dissolved AAm solution was then removed from the water bath—add 5 g glycerol, cover and start degassing/purge with Argon and continue stirring for 5 min.
Add 500 µl of 1% MBA, continue purge and stirring for 5-7 min.
Remove purge line and connect to the covered mold vessel (200 ml PP container w/scrim)
Pipette 250 µl of each diluted catalyst (Per/Bi/Fe) into a 1 ml vial then dispense into the hydrogel solution
Stir for ~15-20 seconds to incorporate and quickly pour into the Argon purged mold-and continue purging Condensation from the polymerized hydrogel was observed within 2 min., purging continued for 15 min. after which the hydrogel with scrim was removed from the mold and placed on a non-stick backing.

Observations: The hydrogel looked good although some bubbles were present, the scrim appeared to be incorporated but the hydrogel may not have been completely uniform on the top and bottom. Dimension's were 8.5 cm in diameter and ~4.5 mm thick. One 8 mm sample was cut from the hydrogel using a punch.

Hydrogel Formulation (3) "Thinner" Ref.5005-1-3 Date May 25, 2012
100 ml tri-pour beaker
12.5 g of acrylamide monomer were dissolved in 7.5 g DI $H_2O$ by placing in a warm water bath ~40° C. while stirring for 10 min.
The dissolved AAm solution was then removed from the water bath—add 5 g glycerol, cover and start degassing/purge with Argon and continue stirring for 5 min.
Add 500 µl of 1% MBA, continue purge and stirring for 5-7 min.
Remove purge line and connect to the covered mold vessel (mold was a Pyrex culture dish 9 cm in dia., the cover was a PP container see photo 5)
Pipette 250 µl of each diluted catalyst (Per/Bi/Fe) into a 1 ml vial then dispense into the hydrogel solution
Stir for ~15-20 seconds to incorporate and quickly pour into the Argon purged mold-continue purging Condensation from the polymerized hydrogel was observed within 2 min., purging continued for 10 min. after which the hydrogel was removed from the mold and placed on a non-stick backing.

Observations: Overall the hydrogel looked good with some small bubbles. Dimension's were 9 cm in diameter and ~3.5 mm thick, slightly thinner than hydrogels of examples 1 and 2.

| Chemical Name | Source | P/N | Lot |
| --- | --- | --- | --- |
| Potassium persulfate | Sigma/Aldrich | P5592 | 77096PJ |
| Potassium bisulfate | Sigma/Aldrich | P2522 | 097K005 |
| Ferrous sulfate | Sigma/Aldrich | F8048 | 030M1777 |
| Acrylamide 99+% | Sigma/Aldrich | 148660 | 01309KE |
| Glycerol 99.5% | Sigma/Aldrich | 32.000-5 | DI04146TU |
| Methylenebis(acryl-amide) | Sigma/Aldrich | 146072 | 4NMKBG3845V |

The above description focuses on oxygenation as merely a representative example. The device has other applications such as CO2 removal, extracorporeal CO2 or ECO2R. A pediatric sized pump oxygenator according to the present invention may be particularly well suited for the adult market for CO2 removal. It may be well suited for removing other gases from blood as desired.

The present invention has been described with the use of the hydrogel packing discussed above, however many of the advantages of the present invention may also be achieved with a swellable packing that is a non-hydrogel. The hydrogel packing is preferred for the advantages discussed above, but a swellable non-hydrogel may come close to the same acceptable operating characteristics.

The preferred embodiments described above are illustrative of the present invention and not restrictive hereof. It will be obvious that various changes may be made to the present invention without departing from the spirit and scope of the invention. The precise scope of the present invention is defined by the appended claims and equivalents thereto.

What is claimed is:

1. An integrated blood pump oxygenator or gas transfer device comprising:
   A central housing member defining a central blood flow path extending along a general longitudinal axis of the integrated blood pump oxygenator or gas transfer device;
   A center pump housing member coupled to the central housing member and defining a pump inlet in fluid communication with the central blood flow path;
   An impeller rotationally received within the area of the pump inlet formed by the central pump housing member, wherein the impeller, inlet and center pump housing member combine to form a centrifugal pump;
   An impeller housing supporting the impeller and wherein the impeller housing and center pump housing member combine to form a rollover outlet in the form of an annular chamber extending around the center pump housing member;
   An outer housing coupled to the impeller housing;
   An annular array of hollow fiber membranes configured for gas transfer within the outer housing; and
   An annular chamber within the annular array of hollow fiber membranes in fluid communication with the annular chamber extending from the impeller around the center pump housing; wherein the annular chamber provides substantially perpendicular radial outward cross flow across the membranes.

2. The blood pump oxygenator or gas transfer device according to claim 1 further including a blood inlet coupling attached to the central housing member and defining a blood inlet path in fluid communication with the central blood flow path.

3. The blood pump oxygenator or gas transfer device according to claim 1 further including an outlet housing coupled to outer housing and defining an annular outlet opening, and a series of communication openings in the outer housing.

4. The blood pump oxygenator or gas transfer device according to claim 3 further including a blood outlet coupling coupled to the outlet housing and which defines a blood outlet path extending downstream of the integrated blood pump oxygenator or gas transfer device.

5. The blood pump oxygenator or gas transfer device according to claim 1 further including a stationary shaft coupled to the impeller housing wherein the impeller is rotationally mounted to the stationary shaft.

6. The blood pump oxygenator or gas transfer device according to claim 5 wherein the shaft extends through the impeller housing.

7. The blood pump oxygenator or gas transfer device according to claim 5 further including bearings between the shaft and the impeller.

8. The blood pump oxygenator or gas transfer device according to claim 7 further including an annular hydrogel impeller packing material adjacent the bearings and around the shaft.

9. The blood pump oxygenator or gas transfer device according to claim 8 further including seal adjacent the annular hydrogel impeller packing material.

10. The blood pump oxygenator or gas transfer device according to claim 9 further including a magnetic drive rotating the impeller.

11. The blood pump oxygenator or gas transfer device according to claim 10 wherein the magnetic drive includes magnets integrated into the impeller.

12. The blood pump oxygenator or gas transfer device according to claim 10 wherein the impeller housing forms an isolation shell between the drive magnet components of the magnetic drive and the impeller magnet components of the magnetic drive and completely separates the liquid side from the drive side in the integrated blood pump oxygenator.

13. The blood pump oxygenator or gas transfer device according to claim 12 further including an outlet housing coupled to outer housing and defining an annular outlet opening, and a series of communication openings in the outer housing.

14. The blood pump oxygenator or gas transfer device according to claim 13 further including a blood outlet coupling coupled to the outlet housing and which defines a blood outlet path extending downstream of the integrated blood pump oxygenator or gas transfer device.

15. An integrated blood pump oxygenator or gas transfer device comprising:
   An outer housing;
   a center pump housing member defining a pump inlet;
   An impeller rotationally received within the area of the pump inlet formed by the central pump housing member, wherein the impeller, inlet and center pump housing member combine to form a centrifugal pump;
   An impeller housing supporting the impeller;
   a stationary shaft coupled to the impeller housing;
   bearings between the stationary shaft and the impeller, wherein the impeller is rotationally mounted to the stationary shaft;

an annular hydrogel impeller packing material adjacent the bearings and around the shaft; and An annular array of hollow fiber membranes configured for gas transfer within the outer housing, and configured such that flow from the centrifugal pump flows over the hollow fiber membranes.

16. The blood pump oxygenator or gas transfer device according to claim 15 further including seal adjacent the annular hydrogel impeller packing material.

17. The blood pump oxygenator or gas transfer device according to claim 15 further including further including a magnetic drive rotating the impeller.

18. The blood pump oxygenator or gas transfer device according to claim 17 wherein the magnetic drive includes magnets integrated into the impeller.

19. The blood pump oxygenator or gas transfer device according to claim 18 wherein the impeller housing forms an isolation shell between the drive magnet components of the magnetic drive and the impeller magnet components of the magnetic drive and completely separates the liquid side from the drive side in the integrated blood pump oxygenator.

20. The blood pump oxygenator or gas transfer device according to claim 19 wherein the impeller housing and center pump housing member combine to form a rollover outlet in the form of an annular chamber extending around the center pump housing member; and further including an annular chamber within the annular array of hollow fiber membranes in fluid communication with the annular chamber extending from the impeller around the center pump housing; wherein the annular chamber provides substantially perpendicular radial outward cross flow across the membranes.

* * * * *